(12) United States Patent
Peter et al.

(10) Patent No.: US 10,590,479 B2
(45) Date of Patent: Mar. 17, 2020

(54) POLYMERASE IDLING METHOD FOR SINGLE MOLECULE DNA SEQUENCING

(71) Applicant: Agilent Technologies, Inc., Santa Clara, CA (US)

(72) Inventors: Brian Jon Peter, Los Altos, CA (US); Joel Myerson, Berkeley, CA (US)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 521 days.

(21) Appl. No.: 15/353,592

(22) Filed: Nov. 16, 2016

(65) Prior Publication Data

US 2017/0067103 A1    Mar. 9, 2017

Related U.S. Application Data

(63) Continuation of application No. 14/538,632, filed on Nov. 11, 2014, now Pat. No. 9,546,398.

(60) Provisional application No. 61/904,262, filed on Nov. 14, 2013.

(51) Int. Cl.
| | |
|---|---|
| *C12Q 1/68* | (2018.01) |
| *C12Q 1/6869* | (2018.01) |
| *C12Q 1/6816* | (2018.01) |
| *C12Q 1/6834* | (2018.01) |

(52) U.S. Cl.
CPC ......... *C12Q 1/6869* (2013.01); *C12Q 1/6816* (2013.01); *C12Q 1/6834* (2013.01)

(58) Field of Classification Search
None
See application file for complete search history.

(56) References Cited

U.S. PATENT DOCUMENTS

| | | | |
|---|---|---|---|
| 6,291,164 B1 * | 9/2001 | Blakesley | C12N 9/1205 435/196 |
| 6,833,246 B2 * | 12/2004 | Balasubramanian | C12Q 1/6869 435/6.1 |
| 7,033,762 B2 | 4/2006 | Nelson et al. | |
| 7,169,560 B2 | 1/2007 | Lapidus et al. | |
| 7,211,414 B2 | 5/2007 | Hardin et al. | |
| 7,223,541 B2 | 5/2007 | Fuller et al. | |
| 7,244,556 B2 | 7/2007 | Sood et al. | |
| 7,256,019 B2 | 8/2007 | Sood et al. | |

(Continued)

OTHER PUBLICATIONS

Fuller et al., The challenges of sequencing by synthesis, Nat Biotechnol. Nov. 2009;27(11):1013-23. Epub Nov. 6, 2009 at p. 1018.*

(Continued)

*Primary Examiner* — Aaron A Priest

(57) ABSTRACT

A method for sequencing a nucleic acid is provided. In certain embodiments the method comprises obtaining a duplex comprising a nucleic acid and a primer, wherein the primer has a nuclease resistant 3' end, combining the duplex with a chain terminator nucleotide and a proof-reading polymerase to produce a reaction in which the polymerase idles on the added chain terminator nucleotide, identifying the chain terminator nucleotide added to the end of the primer; and adding a nuclease-resistant nucleotide to the end of the primer after the polymerase has idled on and removed the added chain terminator nucleotide, thereby producing a duplex comprising the template and an extended primer that has a nuclease resistant 3' end.

20 Claims, 7 Drawing Sheets

(56) References Cited

U.S. PATENT DOCUMENTS

| | | | |
|---|---|---|---|
| 7,645,596 | B2 | 1/2010 | Williams et al. |
| 2003/0134807 | A1* | 7/2003 | Hardin .................. C07H 19/06 514/44 R |
| 2007/0148645 | A1* | 6/2007 | Hoser ..................... B82Y 5/00 435/6.12 |
| 2007/0172859 | A1 | 7/2007 | Hardin et al. |
| 2009/0286245 | A1* | 11/2009 | Bjornson ............. C12Q 1/6869 435/6.18 |
| 2010/0112645 | A1 | 5/2010 | Clark et al. |
| 2010/0330570 | A1 | 12/2010 | Vander Horn et al. |
| 2011/0306504 | A1 | 12/2011 | Xiao et al. |

OTHER PUBLICATIONS

Di Giusto, et al., "Single base extension (SBE) with proofreading polymerases and phosphorothioate primers: Improved fidelity in single-substrate assays", Nucleic Acids Res., 2003, 31(3):e7, 12 pages.

Fuller, et al., "The challenges of sequencing by synthesis", Nature Biotechnology, 2009, 27(11): 1013-1023.

Jo, et al., "A single-molecule barcoding system using nanoslits for DNA analysis", PNAS, 2007, 104(8): 2673-2678.

Wu, et al., "3'-O-modified nucleotides as reversible terminators for pyrosequencing", Proc Natl Acad Sci U S A. Oct. 16, 2007;104(42):16462-7.

\* cited by examiner

POLYMERASE IDLING METHOD FOR SINGLE MOLECULE DNA SEQUENCING

CROSS-REFERENCING

This application is a Continuation of U.S. patent application Ser. No. 14/538,632, filed on Nov. 11, 2014, which claims the benefit of U.S. provisional application Ser. No. 61/904,262, filed on Nov. 14, 2013, all of which applications are incorporated by reference in their entireties.

BACKGROUND

Current methods for DNA sequencing often involve interrogation of many amplified DNA templates on the surface of a bead or slide. Polymerase incorporation of nucleotides can be measured by measuring fluorescence (e.g., Helicos, Illumina technologies) the generation of pyrophosphate (454 technology) or $H^+$ ions (Ion torrent technology). While these methods are rapidly increasing in accuracy and throughput, sequencing technologies that could interrogate a single DNA molecule would obviate the need for DNA amplification of templates, and could potentially enable the detection of DNA modifications such as methylation.

SUMMARY

A method for sequencing a nucleic acid is provided. In certain embodiments the method comprises obtaining a duplex comprising a nucleic acid and a primer, wherein the primer has a nuclease resistant 3' end, combining the duplex with a chain terminator nucleotide and a proof-reading polymerase to produce a reaction in which the polymerase idles on the added chain terminator nucleotide, identifying the chain terminator nucleotide added to the end of the primer; and adding a nuclease-resistant nucleotide to the end of the primer after the polymerase has idled on and removed the added chain terminator nucleotide, thereby producing a duplex comprising the template and an extended primer that has a nuclease resistant 3' end.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
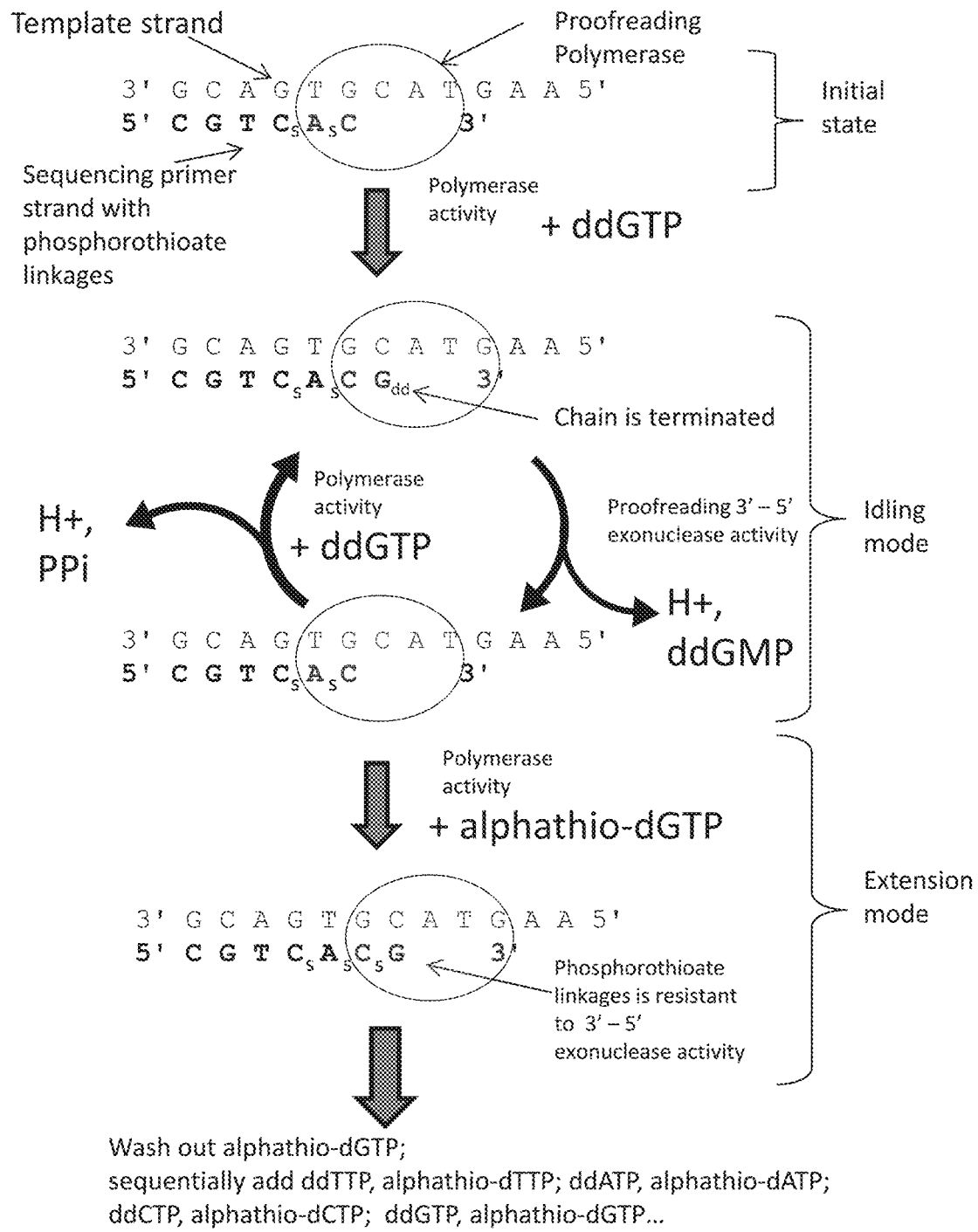
FIG. 1 shows a scheme that utilizes polymerase idling activity to enhance measurement of a DNA sequence. If a polymerase with a proofreading 3'-5' exonuclease activity (such as T4 polymerase or Pfu polymerase) is used, the enzyme will idle in the presence of a single correct nucleotide. When a chain terminator such as ddGTP is used, only a single nucleotide is added, even in homopolymer regions. As the enzyme idles, ddGMP, pyrophosphate, and 2 protons are produced in each idling cycle. If terminal phosphate labeled fluorescent nucleotides are used, a fluorophore will be released in each cycle (not shown.) These byproducts may be measured on existing sequencing platforms. After a suitable amount of time, an exonuclease-resistant "extension nucleotide" is incorporated by the polymerase, and the polymerase moves to the next template nucleotide without idling. Subsequent addition of the appropriate idling nucleotide will enable sequencing of the next base. By sequentially adding modified nucleotides, the sequence of the template strand may be determined.

Before describing exemplary embodiments in greater detail, the following definitions are set forth to illustrate and define the meaning and scope of the terms used in the description.

The term "nucleic acid" and "polynucleotide" are used interchangeably herein to describe a polymer of any length, e.g., greater than about 10 bases, greater than about 100 bases, greater than about 500 bases, greater than 1000 bases, up to about 10,000 or more bases, composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson- Crick base pairing interactions. Naturally-occurring nucleotides include guanine, cytosine, adenine and thymine (G, C, A and T, respectively).

The term "nucleoside" as defined herein is a compound including a purine, deazapurine, or pyrimidine base linked to a sugar or a sugar substitute, such as a carbocyclic or acyclic linker at the 1' position or equivalent position and includes 2'-deoxy and 2'-hydroxyl, 2',3'-dideoxy forms, as well as other substitutions.

The term "nucleoside polyphosphate" as used herein refers to a phosphate ester of a nucleoside, with two or more phosphate groups. Adenosine triphosphate and deoxyguanosine pentaphosphate are examples of nucleoside polyphosphates. Nucleoside polyphosphates may contain chemical groups attached to the terminal phosphate or to internal phosphates. For example, nucleoside polyphosphates may include molecules with an electrochemical label, mass tag, charge blockade label, or a chromogenic label, chemiluminescent label, fluorescent dye, or fluorescence quenching label attached to the terminal phosphate or to an internal phosphate in a polyphosphate chain. Further examples of chemical groups that may be used as labels include chromophores, enzymes, antigens, heavy metals, magnetic probes, phosphorescent groups, radioactive materials, scattering or fluorescent nanoparticles, Raman signal generating moieties, and electrochemical detection moieties. Additionally, the term "nucleoside polyphosphate" as used herein refers to a phosphate ester of a nucleoside, which may comprise imido groups or other modifications to the phosphate chain. For example, adenylyl imidophosphate (AMP-PNP) and deoxycytosine 5'-(gamma-thiotriphosphate) and analogues such as ADP.BeF3 are further examples of nucleoside polyphosphates.

The term "nucleotide" as used herein refers to a phosphate ester of a nucleoside, wherein the esterification site typically corresponds to the hydroxyl group attached to the C-5 position of the pentose sugar. In some cases nucleotides comprise nucleoside polyphosphates. However, the terms "added nucleotide," "incorporated nucleotide," "nucleotide added" and "nucleotide after incorporation" all refer to a nucleotide residue that is part of a oligonucleotide or polynucleotide chain.

The terms "nucleoside", "nucleotide", "deoxynucleoside", and "deoxynucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the "nucleoside", "nucleotide", "deoxynucleoside", and "deoxynucleotide" include those moieties that contain not only conventional ribose and deoxyribose sugars, but other sugars as well. Modified nucleosides, nucleotides, deoxynucleosides or deoxynucleotides also include modifications on the sugar moiety, e.g., wherein one or more of the hydroxyl groups are replaced with halogen atoms or aliphatic groups, or are functionalized as ethers, amines, or the like.

Naturally occurring nucleotides or nucleosides are defined herein as adenine (A), thymine (T), guanine (G), and cytosine (C). It is recognized that certain modifications of these nucleotides or nucleosides occur in nature. However, modifications of A, T, G, and C that occur in nature that affect hydrogen bonded base pairing are considered to be non-naturally occurring. For example, 2-aminoadenosine is found in nature, but is not a "naturally occurring" nucleotide or nucleoside as that term is used herein. Other non-limiting examples of modified nucleotides or nucleosides that occur in nature that do not affect base pairing and are considered to be naturally occurring are 5-methylcytosine, 3-methyladenine, O(6)-methylguanine, and 8-oxoguanine, etc. Nucleotides include any nucleotide or nucleotide analog, whether naturally-occurring or synthetic. Exemplary nucleotides include phosphate esters of deoxyadenosine, deoxycytidine, deoxyguanosine, deoxythymidine, adenosine, cytidine, guanosine, and uridine. Other nucleotides include an adenine, cytosine, guanine, thymine base, a xanthine or hypoxanthine, 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or by being capable of base-complementary incorporation, and includes chain-terminating analogs. A nucleotide corresponds to a specific nucleotide species if they share base-complementarity with respect to at least one base.

In addition to purines and pyrimidines, modified nucleotides or analogs, as those terms are used herein, include any compound that can form a hydrogen bond with one or more naturally occurring nucleotides or with another nucleotide analog. Any compound that forms at least two hydrogen bonds with T or with a derivative of T is considered to be an analog of A or a modified A. Similarly, any compound that forms at least two hydrogen bonds with A or with a derivative of A is considered to be an analog of T or a modified T. Similarly, any compound that forms at least two hydrogen bonds with G or with a derivative of G is considered to be an analog of C or a modified C. Similarly, any compound that forms at least two hydrogen bonds with C or with a derivative of C is considered to be an analog of G or a modified G. It is recognized that under this scheme, some compounds will be considered for example to be both A analogs and G analogs (purine analogs) or both T analogs and C analogs (pyrimidine analogs).

The term "complementary," "complement," or "complementary nucleic acid sequence" refers to the nucleic acid strand that is related to the base sequence in another nucleic acid strand by the Watson-Crick base-pairing rules. In general, two sequences are complementary when the sequence of one can hybridize to the sequence of the other in an anti-parallel sense wherein the 3'-end of each sequence hybridizes to the 5'-end of the other sequence and each A, T, G, and C of one sequence is then aligned with a T, A, C, and G, respectively, of the other sequence. Complementation of modified nucleotide analogs is defined according to the parent nucleotide. Complementation of modified nucleotides analogs does not require the ability to form stable hydrogen bonded base pairs. In other words, two modified nucleotide analogs may be complementary according to the identity of the modified nucleotide analog but may not form a stable base pair. Complementation of nucleotide analogs which are not considered derivatives of A, T, G, or C is defined according to an ability to form a stable base pair with a nucleotide or analog thereof. For example, a particular derivative of C (i.e., 2-thiocytosine) may not form a stable base pair with G, but is still considered complementary.

The term "duplex" means at least two sequences that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base-pairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

The terms "hybridization", and "hybridizing", in the context of nucleotide sequences are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the hybridization of the two sequences. Increased stringency can be achieved by elevating the temperature, increasing the ratio of co-solvents, lowering the salt concentration, and the like.

The terms "hybrid" and "duplex" refer to a double-stranded nucleic acid molecule formed by hydrogen bonding between complementary nucleotides.

The term "primer" means an oligonucleotide, either enzymatically made or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. A primer serves as an initiation point for nucleotide polymerization catalyzed by either DNA polymerase, RNA polymerase or reverse transcriptase. A primer may be 4-1000 bases or more in length, e.g., 10-500 bases.

The term "template" denotes a nucleic acid molecule that can be used by a nucleic acid polymerase to direct the synthesis of a nucleic acid molecule that is complementary to the template according to the rules of Watson-Crick base pairing. For example, DNA polymerases utilized DNA to synthesize another DNA molecule having a sequence complementary to a strand of the template DNA. RNA polymerases utilize DNA as a template to direct the synthesis of RNA having a sequence complementary to a strand of the DNA template. DNA reverse transcriptases utilize RNA to direct the synthesis of DNA having a sequence complementary to a strand of the RNA template.

The phrase "primer extension conditions" denotes conditions that permit for polymerase mediated primer extension by addition of nucleotides to the end of the primer molecule using the template strand as a template.

If a subject primer "corresponds to" or is "for" a certain nucleic acid template, the primer base pairs with, i.e., specifically hybridizes to, that nucleic acid template. As will be discussed in greater detail below, a primer for a particular nucleic acid template and the particular nucleic acid template, or complement thereof, usually contain at least one region of contiguous nucleotides that is identical in sequence.

The term "sequencing" refers to determining the identity of one or more nucleotides, i.e., whether a nucleotide is a G, A, T or C.

The term "obtaining a duplex" refers to a duplex made by, for example: a) hybridizing one nucleic acid (e.g., an oligonucleotide) to another, b) extending a primer that is hybridized to a nucleic acid using the nucleic acid as a template (thereby converting a first duplex that has a first primer into a second duplex that comprises an extended primer) or c) nicking a longer double stranded molecule and then removing nucleotides from the nick site using an exonuclease.

The term "nuclease resistant 3' end" refers to a primer that is resistant to cleavage by a 3' to 5' exonuclease, particularly the 3' to 5' exonuclease activity of a proofreading polymerase. A phosphorothioate linkage is an example of a nuclease-resistant linkage, although others are known. Nuclease resistance may also be conferred by modifications to the base or sugar of the nucleotide, for example 2'-O-methyl nucleotides, 2' Fluoro nucleotides, propyne modified nucleotides, inverted 3'-3' deoxythymidine, etc.

The term "nuclease resistant nucleotide" may refer to a nucleotide that is designed to produce a nuclease resistant linkage (e.g., a phosphorothioate linkage) when it is added to the 3' end of a primer by a polymerase. Nucleoside alpha-thiotriphosphates (see, e.g., Yang et al Nucl. Acids. Res. 2007 35: 3118-3127) are examples of nuclease resistant nucleotides, although others are known. For example, other nuclease resistant nucleotides comprise 2' O-methyl nucleotides, 2' Fluoro nucleotides, propyne modified nucleotides, inverted 3'-3' deoxythymidine, and other modified nucleotides.

The term "chain terminator nucleotide" refers to a nucleotide that cannot serve as a substrate for a nucleotide addition by a polymerase, or is otherwise resist to extension. Dideoxynucleotides, 3' azido nucleotides, and 3' amino nucleotides are examples of chain terminator nucleotides, although many others are known. Other non-limiting examples include 3' phosphate labeled nucleotides, or virtual terminator nucleotides (see, e.g., Bowers et al. Nature Methods 2009 6:593-595.)

The term "reversible chain terminator" is a chain terminator nucleotide that has a blocking moiety that can be removed so that the nucleotide becomes available as a substrate for a polymerase. In some cases, the blocking moiety is on the 3' position, and removal of the blocking moiety yields a 3' hydroxyl. Bentley (Nature 2009 456: 53-59) and Ju (Proc Natl Acad Sci USA. 2006; 103: 19635-19640) describe two examples of chemistry that can be used for reversible chain terminators, though others are known.

The term "proof-reading polymerase" refers to a polymerase that has a 3' to 5' exonuclease activity as well as a polymerase activity, thereby allowing the polymerase to reverse direction, excise a nucleotide, and re-insert another nucleotide at the same position.

The term "idling" refers to a biochemical reaction in which a polymerase repeatedly adds a chain terminating nucleotide and then removes it several times in succession.

The term "identifying" in the context of identifying a chain-terminator nucleotide that has been added to the end of a primer, refers to either determining if a chain terminator nucleotide has been added to the end of the primer and/or determining which type of nucleotide has been added to the end of the primer.

DETAILED DESCRIPTION

Describe herein is a method of DNA sequencing that can be performed on multiple platforms, dramatically increasing the signal generated from reading a single base. In brief, a proofreading DNA polymerase and modified chain-terminator nucleotides "idle" at a single base, undergoing many cycles of incorporation (by the polymerase activity) and digestion (by the 3' to 5' proofreading exonuclease activity) at a single base of the template. Thus, multiple byproducts of nucleotide incorporation and excision (such as pyrophosphate, $H^+$, fluorophores, or other detectable tags) can be generated for a single base. After that base is read with sufficient confidence, a nuclease resistant nucleotide (e.g., a phosphorothioate nucleotide) can be incorporated, which would inhibit the exonuclease activity, allow the polymerase to translocate ahead, and enable the next base to be read. In this fashion, the DNA sequence could be reliably determined from fewer template molecules. In certain cases, the method may allow more signal to be generated from a single base, which may enable accurate single-molecule sequencing. The method may be readily adapted to multiple existing sequencing platforms, depending on whether pyrophosphate, $H^+$, fluorophores, or other tags are measured. In certain cases, the nucleotides used during the idling step may be distinct from those eventually incorporated into the nascent DNA strand; therefore, a variety of labels may be used without altering the properties of the growing template DNA. The method allows homopolymer regions to be accurately sequenced, a single base at a time.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Some of the general principles of the method are illustrated in FIG. 1. The first step of the method (step a) involves obtaining a duplex comprising a nucleic acid and a primer, wherein the primer has a nuclease resistant 3' end. In this step of the method, the duplex may be produced by hybridizing a synthetic primer that contains, e.g., a phosphorothioate linkage at its 3' end, to a template nucleic acid or by addition of a nuclease-resistant nucleotide, e.g., an alpha thiol nucleotide, to the end of a primer that is already hybridized to the nucleic acid. Next, in step b of the method, the duplex is combined with a chain terminator nucleotide (e.g., a dideoxynucleoside triphosphate, but other chain terminator nucleotides may be used) and a proof-reading polymerase (e.g., Pfu, Vent, Deep Vent or T4 DNA polymerase or the like) to produce a reaction in which the polymerase idles on the added chain terminator nucleotide, where the term "idles", as discussed above, means that the polymerase repeatedly adds the chain terminator nucleotide onto the end of the primer using the nucleic acid as a template and then removes it. During or after idling (in step c) the chain terminator nucleotide added to the end of the primer can be identified. As will be discussed in greater detail below, this detection can be implemented in a variety of different ways. Finally, in this implementation of the method, step d of the method involves adding a nuclease-resistant nucleotide to the end of the primer after the polymerase has idled on, and removed, the added chain terminator nucleotide. This step results in a duplex comprising the template and an extended primer that has a nuclease resistant 3' end, and the cycle can be started again. For example in some embodiments, steps (b) and (c) may be repeated on the product of step (d), to determine the sequence of two consecutive nucleotides of the nucleic acid. In these embodiments (and as will be described in greater detail below) the nuclease-resistant nucleotide may be a reversible chain terminator. In these embodiments, the method may involve removing a blocking moiety from the added nuclease-resistant nucleotide after step (d), thereby allowing the polymerase to add a new chain terminator nucleotide to the unblocked reversible chain terminator (allowing step b to be repeated).

In some embodiments, steps (b), (c) and (d) may be repeated at least 10 times, at least 20 times, at least 50 times, at least 100 times, at least 200 times, at least 500 times, or at least 1000 times, thereby determining the sequence of a corresponding number of consecutive nucleotides in the nucleic acid. As would be apparent, different analogs of the same nucleotide (i.e., a chain terminator nucleotide that base pairs with G, A, T or C and a nuclease-resistant nucleotide that base pairs with the same nucleotide) are used in the idling step and in the last step.

As shown in FIG. 1, the method in general contains two steps: a) an idling step (which generates chemical byproducts of nucleotide incorporation and excision) that is initiated using a chain terminator nucleotide and a proofreading polymerase, followed by b) an extension step that results in the addition of a nucleotide via an exonuclease-resistant linkage (e.g., using an alpha-thiotriphosphate nucleoside). The chain-terminators (which may be labeled) that are incorporated and removed in the idling step may be thought of as "signal nucleotides" because, as will be discussed in greater detail below, their incorporation can be detected in a way that indicates the identity of the incorporated nucleotide and the exonuclease-resistant nucleotides can be thought of as "extension nucleotides" because, once they are added, they are not removed and the sequencing reaction can move to the next base. The byproducts generated during the idling mode can accumulate, facilitating measurement to determine whether the correct base was incorporated. Different bases are then cycled through to determine the sequence, as has been described elsewhere (see, e.g., Margulies et al Nature 2005 437: 376-380 as well as many other publications).

In any embodiment, the method may comprise combining said duplex with the chain terminator nucleotide, the proofreading polymerase and the nuclease-resistant nucleotide, wherein the chain terminator nucleotide has a higher probability of being incorporated. For example, in cases where the chain terminator nucleotide and the nuclease-resistant nucleotide have approximately the same probability of being incorporated, incorporation probability can be adjusted by using at least a 2-fold molar excess, at least a 5-fold molar excess, at least a 10-fold molar excess, at least a 50-fold molar excess, or at least a 100-fold molar excess of the chain terminator nucleotide relative to the nuclease-resistant nucleotide. Incorporation probability of a nucleotide or nucleotide analogue may be affected by the binding affinity of the polymerase for the nucleotide, the catalytic efficiency of nucleotide incorporation or turnover, or a combination of both. These parameters may be measured for various enzyme-nucleotide combinations (for example, by methods such as those described in Gardner et al. J. Biol. Chem. 2004 279:11834-11842, Anderson et al. Biotechniques 2005 38: 257-264, and references therein.) After relative incorporation probabilities of various idling and extension nucleotides have been measured, the relative concentrations or reaction conditions may be adjusted to achieve the desired ratio of idling nucleotides to extension nucleotides. In these embodiments, the polymerase will typically incorporate multiple idling nucleotides (and generate signal) before incorporating an extension nucleotide and moving to the next base in the template. If the polymerase has a lower incorporation efficiency for the extension nucleotides, the concentrations or molar ratios could be adjusted to ensure a higher probability of incorporating chain terminator nucleotides (i.e., idling nucleotides) versus nuclease-resistant nucleotides (i.e., extension nucleotides). In addition to adjusting concentrations, polymerase reaction conditions such as buffer, pH, temperature, salt concentration, etc., may be varied to alter the relative probabilities of incorporating chain terminator nucleotides versus extension nucleotides. The effect of these reaction conditions on incorporation probabilities can be measured using the techniques outlined in the publications cited above.

As would be apparent, in some embodiments, the amount of chain terminator nucleotide added to the end of the primer (i.e., the number of cycles of idling) may be quantified.

In particular cases, a single reaction cycle may be done using a single nucleotide (i.e., a nucleotide corresponding to G, A, T or C) and the method involves detecting whether a nucleotide is incorporated. If a nucleotide is incorporated, then the identity of the nucleotide becomes known. In these embodiments, the method may involve cycling through all four nucleotides (i.e., nucleotides corresponding to G, A, T and C) in succession and one of the nucleotides should be incorporated. In these embodiments, the addition of the nucleotide may be detected by detecting pyrophosphate release, proton release or fluorescence, for example, methods for which are known. For example, in some embodiments, the chain terminator nucleotide may be a terminal phosphate labeled fluorescent nucleotide (i.e., a nucleotide that has a fluorophore attached to the terminal phosphate) and the identifying step comprises reading fluorescence. In other embodiments, the chain terminator nucleotide may be a fluorescent nucleotide that comprises a quencher on a terminal phosphate. In these embodiments, incorporation of the nucleotide removes the quencher from the nucleotide, thereby allowing the fluorescent label to be detected. In other embodiments, the terminal phosphate labeled chain terminator nucleotide may be labeled on the terminal phosphate with a mass tag, charge label, charge blockade label, chemiluminescent label, redox label, or other detectable label.

In other embodiments, a single reaction cycle may be done using all four nucleotides (i.e., nucleotides corresponding to G, A, T and C), each labeled with different fluorophores. In these embodiments, the combining step (b) may comprises combining the duplex with four chain terminators corresponding to G, A, T and C, wherein the four chain terminators comprise different fluorophores. In these embodiments, the identifying step (c) may comprise identifying which of the four chain-terminator is added to the end of the primer.

As will be described in greater detail below, in some embodiments, the duplex may be a DNA molecule that comprises single stranded regions and double stranded regions, that has been stretched on a substrate, e.g., in a nanofluidic channel on a substrate. In these embodiments, the duplex may be made by: nicking a double stranded DNA (e.g., a double stranded DNA that may be of, e.g., at least 1 kb, at least 10 kb, at least 50 kb, at least 100 kb or at least 10,000 kb in length, at one or more sites, then making single stranded gaps in the double stranded DNA using an exonuclease. In these embodiments, the ends of the double stranded regions (which function as primers) may be made nuclease-resistant by adding an, e.g., alpha-thio reversible terminator, onto 3' ends adjacent to the gaps. The primers can be activated by deprotecting the added alpha-thio reversible terminators. In these embodiments, the exonuclease may be ExoIII. The nucleic acid or the primer may be immobilized on a solid support.

In certain cases the method may be used to sequence a homopolymeric region (i.e., a sequence containing a contiguous sequence of 2, 3, 4, 5, 6, or 7 or more of the same nucleotide). Although the idling mode uses chain terminator nucleotides, the extension mode must use nuclease resistant nucleotides that can eventually be added to. Therefore, in homopolymer regions, several nuclease resistant nucleotides could be added during the extension mode and the signal may not be recorded. The number of added nucleotides can be determined using several different methods, two of which are described below.

The first method for sequencing homopolymeric regions uses a nuclease resistant nucleotide (e.g., an alpha-thio-dNTP) that has a reversible chain-terminator modification. When the reversibly blocked chain terminator is added, the chain terminator modification will block further incorporation, enabling homopolymers to be sequenced one base at a time (see, e.g., Wu, J., S. Zhang, et al. (2007). "3'-O-modified nucleotides as reversible terminators for pyrosequencing." Proc Natl Acad Sci USA 104(42): 16462-16467). After each incorporation, the chain terminator modification could be reversed by chemical, biochemical or photochemical means, allowing the addition of further nucleotides. For example, the chain terminator may comprise a photocleavable chemical group which blocks polymerase extension before cleavage, but allows polymerase extension after photocleavage. For example, the chain terminator may comprise a 3' phosphate group which blocks extension, but which is subsequently removed by chemical means or by a phosphatase activity.

The second method for sequencing homopolymeric regions can be applied when many copies of the same sequence are being sequenced (as in current Ion torrent, 454 pyrosequencing, and Illumina reversible terminator sequencing technologies.) If many copies of the same DNA molecule are being sequenced, a mixture of nuclease resistant nucleotides (e.g., alpha-thio-dNTPs) and chain terminators (e.g., ddNTPs) can be added to the polymerase, typically with a higher ratio of signal nucleotides to extension nucleotides. For example, if chain terminator nucleotides and the nuclease resistant nucleotides have equal probability of incorporation, and the template has a run of 3 Thymidine residues, a mixture of ddATP and alpha-thio-dATP at a ratio of at least 10:1, at least 50:1, at least 100:1, or at least 500:1 ratio can be added. In this case, if the signal nucleotides are several-fold more abundant, in most cases the polymerase will add a chain terminator nucleotide, and persist in idling mode. Occasionally, the polymerase will add a nuclease resistant nucleotide and move to the next base, where it is likely to incorporate more terminator nucleotides in idling mode. Eventually three nuclease resistant nucleotides (e.g., alpha-thio-dATPs) will be incorporated, and no more signal will be generated. Although each individual template may add the chain terminators at a different time, the ensemble of template copies should show a consistent amount of signal generated per base in the homopolymer. Thus, a run of 3 T residues in the template should generate three times as much signal (and generate signal for three times as long) as a single T in the template. Homopolymer runs are then resolved by integrating the signal generated as each mixture of chain terminator and nuclease resistant nucleotides is added, in a similar fashion to methods described by 454 or Ion Torrent technologies. In some embodiments, nucleotides without chain terminators may be used in the idling step. In these embodiments, multiple signal nucleotides may be added, and removed, in a homopolymer region before the extension nucleotide is added. Even in this case, the average data for the ensemble should be consistent for a homopolymer of a given length, and the extra signal afforded by polymerase idling may increase accuracy of sequence determination. In cases where the idling nucleotides and the extension nucleotides have different probabilities of being incorporated (for example, if the extension nucleotides are incorporated more readily or at a lower concentration than the idling nucleotides), relative concentrations of idling and extension nucleotides may be adjusted to provide enough signal from the idling nucleotides before an extension nucleotide is incorporated and the polymerase moves on to the next base. In some embodiments, it may be advantageous to adjust the relative probabilities of incorporating signal nucleotides versus extension nucleotides. The preferred ratio of incorporation may depend on the application. For example, if high accuracy is desired, or in cases where signal is low (e.g., single molecule sequencing), it may be advantageous to ensure the polymerase incorporates and removes at least 5, at least 10, at least 100, at least 1000, or more idling nucleotides before incorporating an extension nucleotide. In contrast, if sequencing speed is desired, it may be advantageous to use conditions which favor fewer cycles of idling before an extension nucleotide is incorporated. In some embodiments, it may be possible to measure the signal from the idling nucleotides in real time and adjust reaction conditions to switch to extension nucleotides once enough signal has been measured. In any embodiments, variants of DNA polymerase may be used. Strong proofreading polymerases such as T4 polymerase, Vent polymerase, or Pfu polymerase may be used when a higher exonuclease activity is desired, while enzymes with weaker proofreading activity such as Klenow fragment may be advantageous if less exonuclease activity is needed. Alternatively, the 3'-5' exonuclease activity may be supplemented or completely supplied by a different enzyme, such as ExonucleaseIII, in which case a non-proofreading polymerase may be used. DNA polymerases useful in the invention include, but are not limited to: *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), Stoffel fragment, ThermoSequenase™ (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 2001/0132887), *Pyrococcus* GB-D (PGB-D) DNA polymerase (also referred as Deep Vent™ DNA polymerase (Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *Thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J Biol. Chem. 256: 3112), and archaeal DP1I/DP2 DNA polymerase II (Cann et al., 1998, Proc Natl Acad. Sci. USA 95:14250).

In particular cases, the polymerase may be a polymerase that has been selected specifically because it has high affinity for the above-described nucleotide analogs and/or an altered 3' to 5' exonuclease activity. Different mutants of the polymerase, exonuclease and/or pore proteins could be used to optimize the discrimination of the pore and the efficient incorporation of idling and extension nucleotides.

In certain embodiments, a polymerase may be subjected to so-called "directed evolution" methods that select for a polymerase with altered affinity for the substrates described above and/or altered exonuclease activity. A variety of such directed evolution methods are known in the art, including but not limited to DNA shuffling (PCT WO 00/42561 A3; PCT WO 01/70947 A3), exon shuffling (U.S. Pat. No. 6,365,377; Kolkman & Stemmer, 2001, Nat Biotechnol 19:423-428), family shuffling (Crameri et al., 1998, Nature 391:288-291; U.S. Pat. No. 6,376,246), RACHITT (Coco et al., 2001, Nat Biotechnol 19:354-359; PCT WO 02/06469), STEP and random priming of in vitro recombination (Zhao et al., 1998, Nat Biotechnol 16:258-261; Shao et al., 1998, Nucleic Acids Res 26:681-683), exonuclease mediated gene assembly (U.S. Pat. Nos. 6,352,842; 6,361,974), Gene Site Saturation Mutagenesis™. (U.S. Pat. No. 6,358,709), Gene Reassembly™ (U.S. Pat. No. 6,358,709), SCRATCHY (Lutz et al., 2001, Proc Natl Acad Sci USA 98:11248-11253), DNA fragmentation methods (Kikuchi et al., Gene 236:159-167), single-stranded DNA shuffling (Kikuchi et al., 2000, Gene 243:133-137), and AMEsystem™ directed evolution protein engineering technology (Applied Molecular Evolution) (U.S. Pat. Nos. 5,824,514; 5,817,483; 5,814,476; 5,763,192; 5,723,323).

Figure 2:
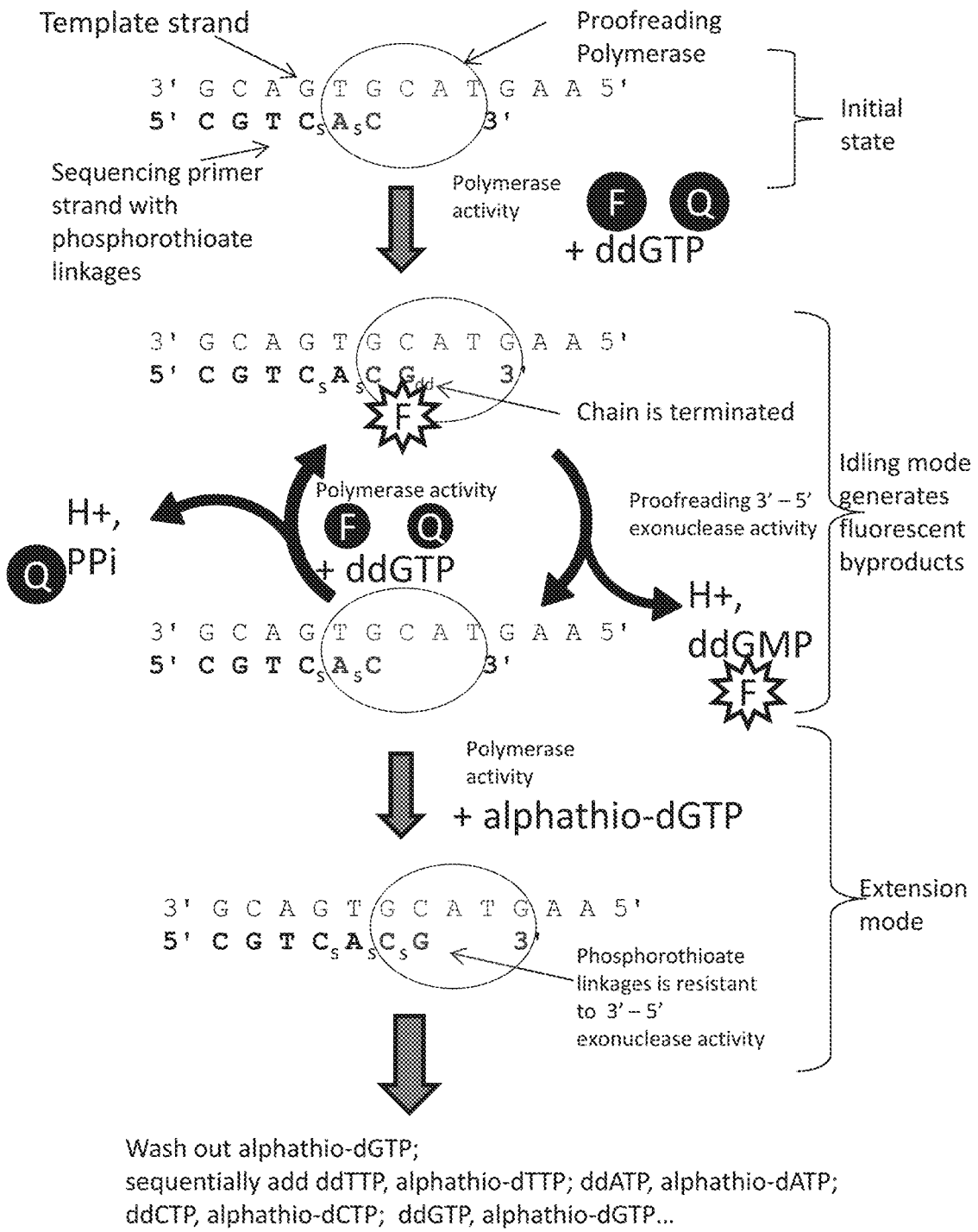
FIG. 2 shows a scheme that utilizes polymerase idling and quenched-fluorescent nucleotides. In this embodiment, nucleotides with a fluorophore on the base (or 3' or 2' position of the sugar) are quenched by a quencher group attached to the terminal phosphate. Upon incorporation of the nucleotide, the quencher-phosphates are removed, and the incorporated nucleotide becomes fluorescent. As the enzyme idles, fluorescent ddGMP, pyrophosphate, and two protons are produced in each idling cycle. After the fluorescence is recorded, nuclease-resistant nucleotides such as alpha-thiotriphosphate nucleosides are added in the extension mode. These extension nucleotides may also have a reversible terminator group (not shown) to facilitate accurate sequencing through homopolymer regions. By sequentially adding 4 modified idling nucleotides, and 4 modified extension nucleotides, the sequence of the template strand may be determined.

In some cases it may be advantageous for fluorescence to be generated only after a polymerase has incorporated a nucleotide base. One way to do this is for a quencher to be released from a fluorescent nucleotide during the addition. Combining quenched-fluorescent nucleotides with polymerase idling will result in multiple fluorophores generated for each single base extension. This embodiment is illustrated in FIG. 2. Other related embodiments may have the fluorescent label attached to a phosphate group (which may or may not be the terminal phosphate), and a fluorescence quenching group on the base.

The method generally described above can be adapted to various sequencing platforms. For example, the method can be adapted to utilize Ion Torrent technology, which uses semiconductor technology to detect protons released by nucleotide incorporation (see, e.g., Rothberg et al. An integrated semiconductor device enabling non-optical genome sequencing. Nature 2011 475: 348-352). Notably, with polymerase idling, a single proton is released during incorporation and another proton is released during nucleotide excision, thus two protons are produced per idling cycle. Signal amplification from the idling step, combined with the production of 2 protons per idling cycle, may significantly increase the amount of signal generated from each template molecule. In some embodiments, enough signal may be generated from each template to enable semiconductor-based sequencing of a much smaller number of DNA templates per sensor, potentially extending to enable sequencing of single molecules. In these embodiments, a single DNA molecule can be affixed directly to the proton-sensitive surface of the substrate, eliminating the use of beads and potentially enabling a higher density of different template molecules, though this may depend on the electronics required for accurate proton detection. In these embodiments, it may be advantageous to attach a single, specific primer sequence to the surface, thereby capturing a template DNA molecule by hybridization. The polymerase idling and extension steps could then occur close to the substrate surface, generating many protons that would create the signal indicating incorporation of a specific base. If specific primers for a region of interest are used, this would enable targeted sequencing of the region of interest.

The added nucleotide can be detected using a variety of other methods. For example, in another embodiment, pyrophosphate release could be measured, and the DNA sequence can be determined by sequential addition of different nucleoside triphosphates (see. e.g., Liu, D. J., G. M. Credo, et al. (2011). "Surface immobilizable chelator for label-free electrical detection of pyrophosphate." Chem Commun (Camb) 47(29): 8310-8312). In another embodiment, modified tetraphosphate nucleotides could be incorporated to generate an ATP molecule in each cycle, and the ATP could be detected in a subsequent reaction with an enzyme such as firefly luciferase (see, e.g., U.S. Pat. No. 7,682,809). In another embodiment, microcalorimetric detection of the heat generated by incorporation of the nucleotide could be used to determine the sequence (see, e.g., U.S. Pat. No. 7,645,596). Each of these embodiments would benefit from the multiple byproducts of incorporation that are generated as each base is read multiple times in idling mode.

Another embodiment of the method can be implemented on the Pacific Biosciences platform (Eid, J., A. Fehr, et al. (2009). "Real-time DNA sequencing from single polymerase molecules." Science 323(5910): 133-138). In this embodiment, the chain terminator used in the idling mode could be a terminal phosphate-labeled fluorescent nucleoside such that the fluorophore would be released upon incorporation and detected by the zero-mode-waveguide. Alternatively, modified nucleotides or nucleotide analogs with fluorescent groups linked either to the base or to the sugar could be used, as the incorporated fluorophore will be removed by the exonuclease activity and a non-fluorescent nucleotide can be used for extension. In the current implementation of the Pacific Biosciences SMRT sequencing platform, there is only one chance per nucleotide to record the fluorescence resulting from incorporation. In the present method, the polymerase could dwell in idling mode, generating fluorophores from the signal nucleotides until the identity of the base is reliably detected. Then, the exonuclease resistant nucleotide (e.g., an exo-resistant nucleoside triphosphate) could be added, and the chain could be extended. In one embodiment, a mixture of 4 chain terminator nucleotides (e.g., chain terminator terminal-phosphate-labeled fluorescent nucleosides corresponding to A, C, T, and G, or nucleosides with 3, 4, 5, 6 or more phosphates, where the fluorescent molecule is attached to the $2^{nd}$, $3^{rd}$, $4^{th}$, $5^{th}$, or terminal phosphate) may be added to many single molecule templates in separate zero mode waveguides, and signals are recorded during polymerase idling. Then, a mixture of 4 nuclease resistant nucleotides (e.g., alpha-thiotriphosphate nucleosides with reversible terminator groups) can be added in the extension mode. Finally, the terminators can be cleaved and the mixture of chain terminator nucleotides is added again to enable reading of the next base.

In some embodiments, the reversible terminator group on the extension nucleotide may be labeled with a fifth fluorescent label, distinct from the fluorescent labels used on the chain terminator idling nucleotides. Alternatively, a fifth fluorescent label could be used on a phosphate group that is cleaved during incorporation of the nuclease resistant extension nucleotide. The fifth fluorescent label (which may be the same for all 4 extension nucleotides) would serve as an "index" to indicate when an extension nucleotide is incorporated. In some cases, it may be possible to use a mixture of 4-color-labeled idling nucleotides with extension nucleotides labeled in a $5^{th}$ (or $5^{th}$ and $6^{th}$, or $5^{th}$, $6^{th}$, and $7^{th}$, or $5^{th}$, $6^{th}$, $7^{th}$, and $8^{th}$) color(s), such that the fluorescence from idling nucleotides can be used to discriminate sequence, and the fluorescence from the extension nucleotides will indicate when the polymerase has moved to the next base in the template.

In another embodiment that could be implemented on the Pacific Biosciences platform, a further advantage could be obtained by incorporating two different dyes (one on the terminal phosphate and the other on the nucleoside). In this embodiment, when a nucleotide is added and excised, there should be a characteristic pattern of a one color flash (terminal phosphate dye released), a longer second color fluorescence (the incorporated nucleotide), followed by a dark phase period of no signal (the excision of the nucleotide). This pattern will repeat with every idling cycle. Filtering for the presence of this pattern could help significantly increase the signal to noise of the measurement and the ultimate reliability of detection.

As noted above, in certain embodiments, a mixture of fluorescent chain terminator (idling nucleotides) and fluorescent or unlabeled, reversible chain terminator nucleotides could be used. In these embodiments, if the probability of incorporating the idling nucleotides is high relative to the probability of incorporating the extension nucleotides (e.g., >10 fold higher) the polymerase may idle on a single base, generating many fluorophores that can be detected to determine the sequence of the template at that position. After a number of idling cycles, an extension nucleotide will be incorporated. Incorporation of the extension nucleotide can be detected as a loss of signal from that molecule. Alternatively, if the idling nucleotides have two fluorescent labels, one on the base and one on the terminal phosphate as described above, the extension nucleotide could contain a label only on the terminal phosphate Thus, incorporation of the extension nucleotide could be detected as the signal of the release of the terminal phosphate dye, in the absence of the signal from the base. In these embodiments, it may be advantageous to label the extension nucleotide with a label of a different color than the idling nucleotides.

Thus, this method could increase the sensitivity of the Pacific Biosciences SMRT sequencing method, because multiple fluorophores can be generated per base read. This method should increase the accuracy of the instrument since incorporation events can be more reliably read by multiple fluorophores. Finally, this method also increases the versatility, since fluorophores could be attached to the sugar, base, or phosphate groups.

In some embodiments, polymerase idling may avoid some of the disadvantages of using reversibly terminated fluorescent nucleotides for single molecule sequencing (e.g. as demonstrated by Helicos' sequencing technology). Due to the stochastic nature of fluorescence, quenching, bleaching, and blinking, it can sometimes be difficult to detect fluorescence from a single fluorophore (see, e.g., Fuller, C. W., L. R. Middendorf, et al. (2009). "The challenges of sequencing by synthesis." Nat Biotechnol 27(11): 1013-1023). In some cases, the single fluorophore may be destroyed before one has a chance to detect it, and perhaps more significantly, many dyes are often very difficult to get greater than 90% pure, and 99% purity can be considered exceptional. For non-single molecule techniques this is not a significant problem. But for single molecule sequencing by synthesis, a dye purity of 90% translates to a potential error rate of 10%. With the addition of polymerase idling, a fresh fluorophore is created with each idling step, greatly increasing the likelihood that a single base extension on a single molecule will be reliably detected.

The method described above can also be adapted for pyrosequencing, as exemplified by 454 technology (Margulies, M., M. Egholm, et al. (2005). "Genome sequencing in microfabricated high-density picolitre reactors." Nature 437 (7057): 376-380). In 454 methods, the pyrophosphate produced by the enzyme is converted to ATP by sulfurylase, and the ATP is used by the enzyme luciferase to produce light, which is detected by a CCD camera. One drawback of the 454 technology is that homopolymer sequences can be difficult to sequence accurately, as multiple nucleotides may be incorporated simultaneously. In using the present method, multiple pyrophosphates can be produced in idling mode, amplifying the signal produced by incorporation of a base. However, in the current method, the use of a chain terminator during idling mode and a reversible chain terminator for the extension nucleotide ensures that only one nucleotide is incorporated at a time, thus enabling accurate sequencing of homopolymer regions.

Nucleic acids have also been analyzed using biological or solid state nanopores (reviewed in, e.g., Venkatesan, B. M. and R. Bashir (2011). "Nanopore sensors for nucleic acid analysis." Nat Nanotechnol 6(10): 615-624). Although naked DNA or RNA can transport through a nanopore at speeds that are sometimes too fast for the measurement of individual bases, the use of a translocating enzyme may enable pore translocation at speeds slow enough for sequencing. Several groups have made progress analyzing DNA using exonuclease (see, e.g., Clarke, J., H. C. Wu, et al. (2009). "Continuous base identification for single-molecule nanopore DNA sequencing." Nat Nanotechnol 4(4): 265-270) or various DNA polymerase enzymes (see, e.g., Lieberman, K. R., G. M. Cherf, et al. (2010). "Processive replication of single DNA molecules in a nanopore catalyzed by phi29 DNA polymerase." J Am Chem Soc 132(50): 17961-17972).

Use of the present method could enhance the ability of nanopore sensors to accurately read a DNA base. For example, a DNA polymerase attached to a template strand could engage an alpha-hemolysin-based pore in a membrane, such that the single stranded region extends through the pore. As modified nucleotides are added and removed in idling mode, the enzyme will translocate the DNA strand back and forth through the nanopore, allowing reading of a base or motif of several bases in the pore. Once that base or motif is read with sufficient confidence, addition of extension nucleotides will allow nucleotide addition and translocation, enabling the reading of the next base or motif. In embodiments, the polymerase could be incubated with a mixture of extension and idling nucleotides, such that there is a high probability of idling on each base before the extension nucleotide is added. Idling nucleotides could cause the DNA to linger at the nanopore entrance long enough to read the base or motif with confidence.

Alternatively, the nanopore could be used to measure nucleoside monophosphates released by an exonuclease (Clarke, Wu et al. 2009, supra). One drawback of exonuclease-based nanopore sequencing methods is that the nucleoside monophosphates released by an exonuclease activity may transit the pore too quickly to detect, or some of the released bases may diffuse away from the pore instead of entering it. If the exonuclease activity is supplied by a polymerase with proofreading, multiple nucleoside monophosphates would be released by the idling enzyme at each base position, increasing the probability of detection. When an extension nucleotide is eventually incorporated, the polymerase will translocate and enable reading of the next base. If an extension nucleotide with a reversible terminator is used, the terminator could be removed by photoactivation or by chemical means.

In order for polymerase idling to occur in these methods, nucleoside triphosphates may need to be present in solution at a reasonable concentration. Because some fraction of these free floating nucleoside triphosphates would also traverse the pore, it may be important for the pore to distinguish between nucleoside monophosphates that have been cleaved by the nuclease, and nucleoside triphosphates which have not yet been incorporated and cleaved by the idling mechanism. This could be accomplished rather easily by coupling a large tag on the terminal phosphate group of the free floating nucleoside triphosphates. When a nucleoside triphosphate with an attached tag translocates through the pore, the current blockade will be a sum on the current blockade from the nucleoside triphosphate and the tag. These will be perfectly correlated in time. When a nucleoside monophosphate with no tag passes through the pore, the signal will be much different in character. The signal for an untagged nucleoside monophosphate will likely be smaller than the signal for tagged nucleotides, but it will still be sufficiently strong for determination of the nucleotide type.

Two mechanisms for missing a nucleoside monophosphate exist. Firstly, once a nucleoside monophosphate is cleaved by the exonuclease, it has a non-zero probability of diffusing away from the pore and thus not translocating through it. Previous exonuclease approaches could not tolerate such a source of error, since this meant that a deletion would necessarily be read in the final sequence. Nucleoside monophosphates lost through diffusion could be tolerated by our approach, however, since many nucleoside monophosphates are generated while the polymerase idles over each base. Secondly, even if an exonuclease cleaved nucleoside monophosphate travels through the pore, it will still be possible to miss it, should a free floating tagged nucleoside triphosphate traverse the pore at nearly the same time, thus masking the smaller signal of the nucleoside monophosphate. Again, this type of missed signal could be tolerated in our approach since many nucleoside monophosphates will be generated for each base of sequence, and at least some will traverse the pore alone.

In some embodiments, single DNA molecules may be sequenced in a nanofluidic channel. Sequencing single DNA molecules elongated in a nanofluidic channel could have advantages of specifically localizing several regions of sequence along a long DNA template. Thus, several sequences from a single DNA haplotype may be obtained in parallel. However, nanofluidic sequence determination methods typically obtain sequence from a single molecule, and thus require detection of a single fluorophore. The present method enables generation of multiple signals from each base that is sequenced, allowing efficient sequencing of several regions of long DNA molecules.

Figure 4:
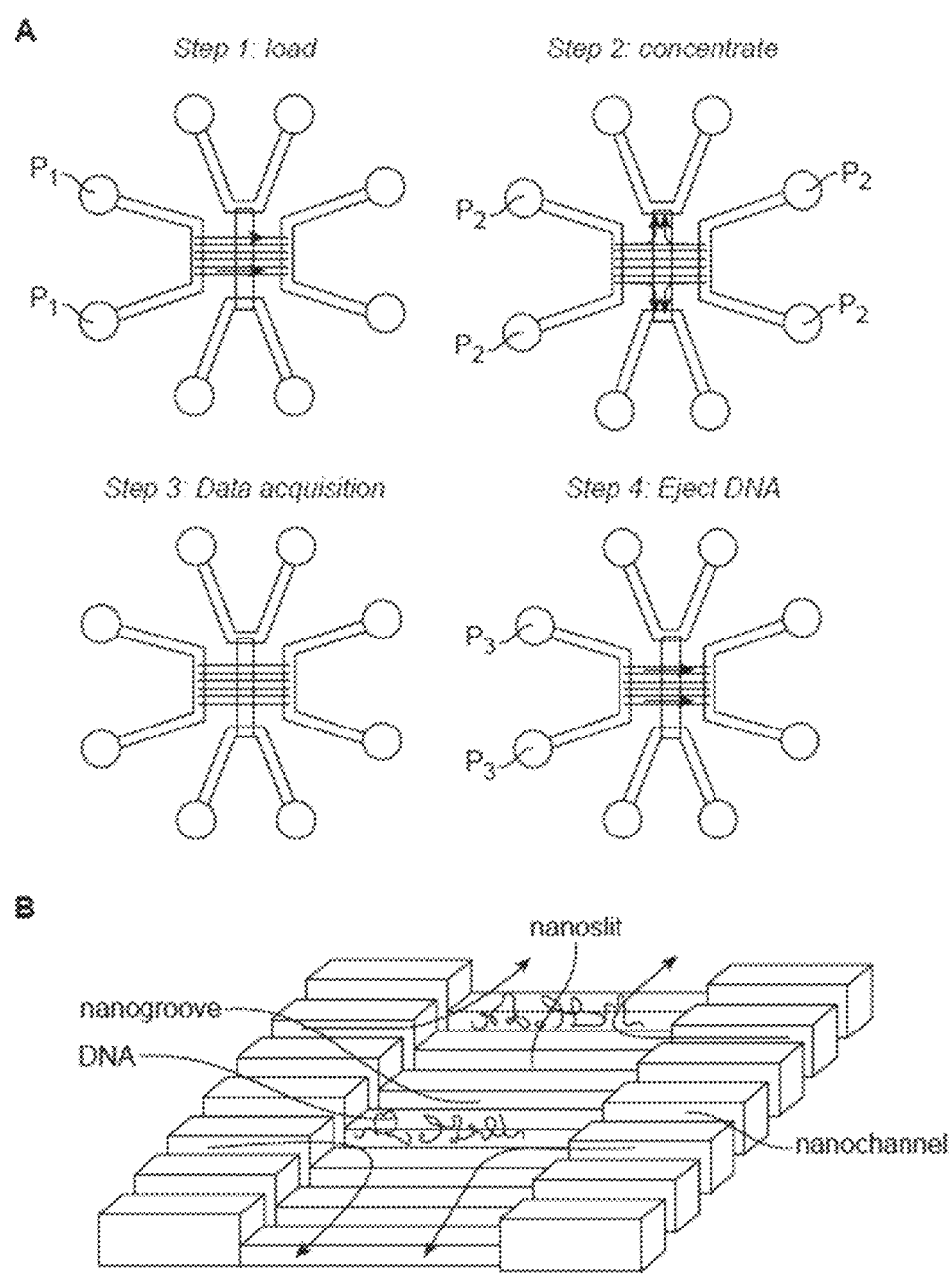
FIG. 4 shows a method for sequencing in nanofluidic channels A. Channel design described by, e.g., Reisner et al (Proc. Natl. Acad. Sci. 2010 107: 13294-13299) allows introduction of buffer (and reagents such as polymerase and nucleotide analogs) into the nanochannel where the long DNA remains trapped by entropic forces.
Figure 5:
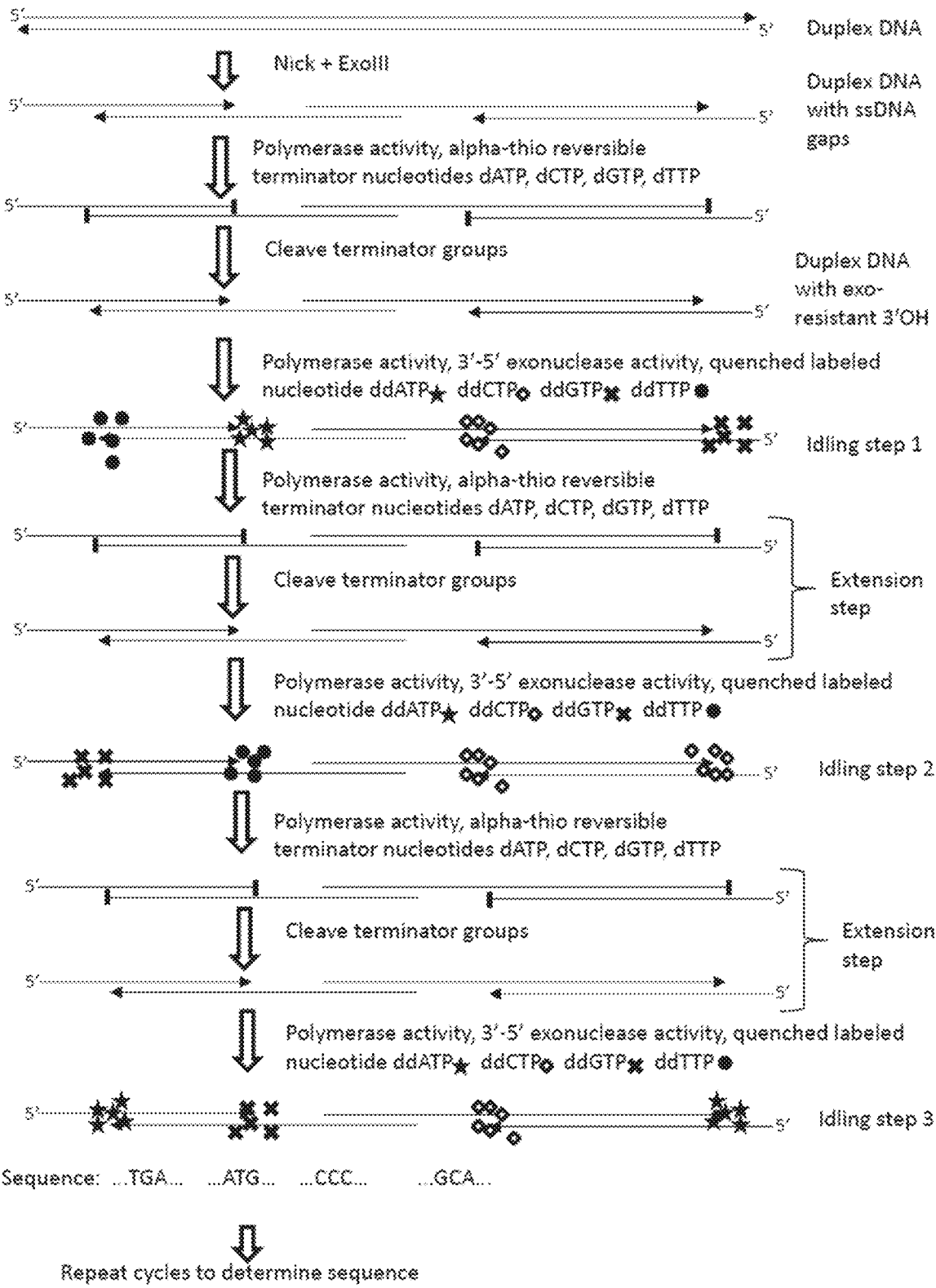
FIG. 5 illustrates a method for sequencing long DNA in a nanofluidic channel or on a solid substrate.
Figure 6:
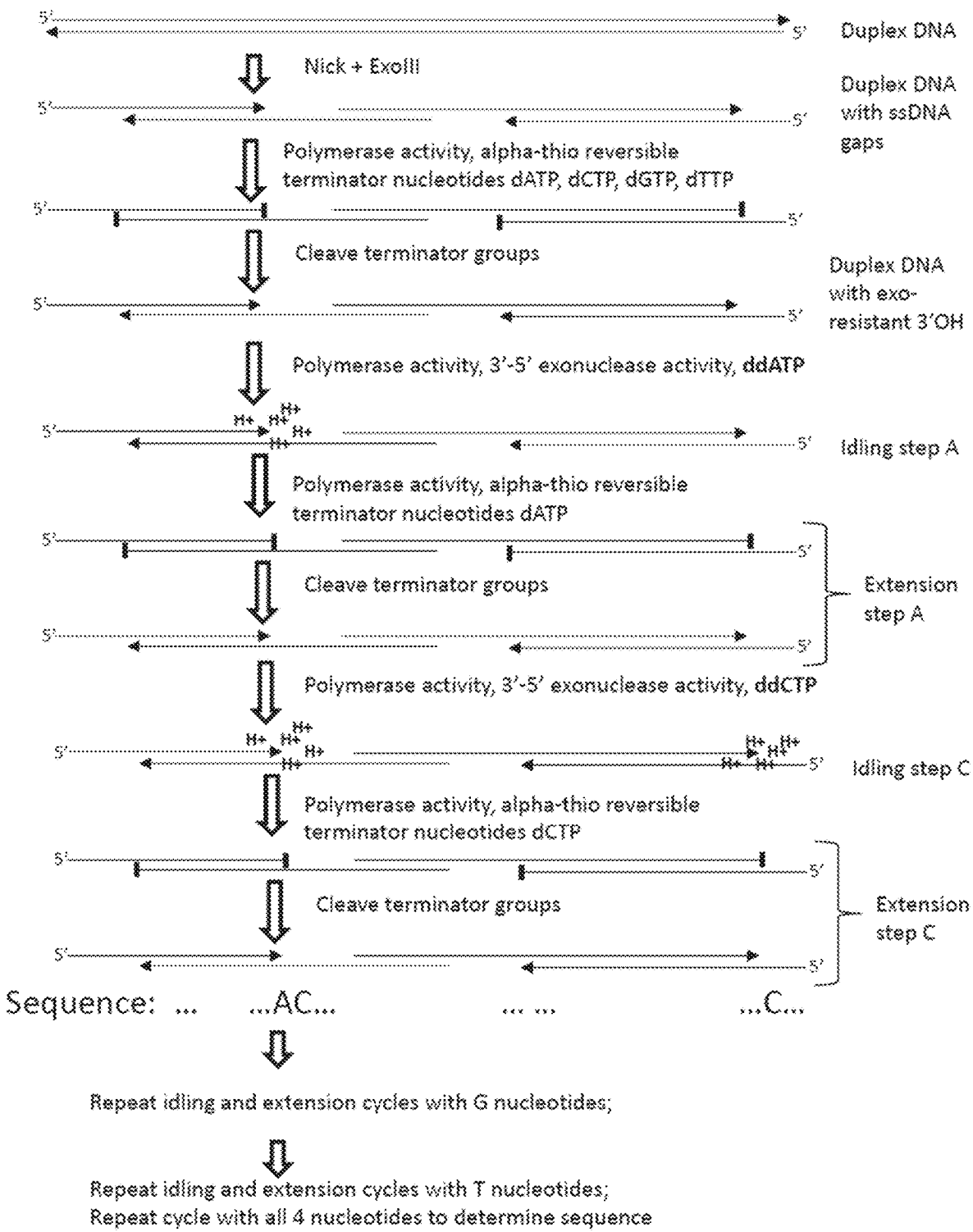
FIG. 6 illustrates a method for sequencing long DNA by measuring pH during the idling step, for example with a hydrogen sensitive ISFET embedded in a nanochannel.

In another embodiment, as shown in FIGS. 5 and 6, single DNA molecules could be sequenced while elongated in nanofluidic channels (see, e.g., Tegenfeldt, J. O., C. Prinz, et al. (2004). "From the Cover: The dynamics of genomic-length DNA molecules in 100-nm channels." Proc Natl Acad Sci USA 101(30): 10979-10983; Reisner, W., N. B. Larsen, et al. (2010). "Single-molecule denaturation mapping of DNA in nanofluidic channels." Proc Natl Acad Sci USA 107(30): 13294-13299). After duplex DNA is introduced into nanochannels, the DNA sequence could be obtained at single stranded breaks, or nicks, in the DNA duplex. In some embodiments a nanochannel or nanogroove device allowing flow or diffusion of reagents (shown in FIG. 4) may be used, so that nucleotides could be cycled. In such a device, elongated DNA molecules remain in the nanochannels, while the "roof" of the nanochannels contains either a nanoslit or a porous region allowing smaller molecules (such as modified nucleotides or nucleotide analogs, or enzymes) to pass through. Reagents can then be introduced into the nanochannel by a pressure gradient, and allowed to accumulate in the nanochannel during idling mode. Then, the extension nucleotides can be introduced, allowing extension and subsequent reading of the next base.

In some embodiments, the sequence of DNA in a nanofluidic channel could be measured electronically. Methods of electronic detection of DNA in nanochannels have been described (see, e.g., U.S. Pat. No. 6,833,246) and, separately, ISFET devices for electronic detection of chemicals have also been described (see, e.g., Bergveld, P. (2003). "Thirty years of ISFETOLOGY: What happened in the past 30 years and what may happen in the next 30 years". Sensors and Actuators B: Chemical 88 (1): 1-20). ISFET detection has been implemented by Ion Torrent Inc., whose DNA sequencing technology is described in detail elsewhere (see, e.g., Rothberg, J. M., W. Hinz, et al. (2011). "An integrated semiconductor device enabling non-optical genome sequencing." Nature 475(7356): 348-352). In summary, field effect transistors (FETs) are buried within their sensing chips. Metal vias extend from each transistor gate to an extended gate electrode which lies just under the wafer surface. This electrode is passivated with a thin dielectric of alumina and a second thin dielectric layer of Tantalum oxide, chosen due to its sensitivity to hydrogen ion concentration. These sensors, located at the bottom of microwells, detect a cloud of $H^+$ ions produced each time bases are incorporated in the DNA located in that well. Theoretically nanofluidic channels could be constructed with similar hydrogen sensitive ISFET devices integrated along each channel at multiple points. Additionally, ISFET detectors with layers sensitive to other chemical species, such as pyrophosphate (Liu, D. J., G. M. Credo, et al. (2011). "Surface immobilizable chelator for label-free electrical detection of pyrophosphate." Chem Commun (Camb) 47(29): 8310-8312.) could be incorporated, increasing the number of replication products that could be detected. When compared with the conventional methods, the concept of embedding multiple ISFET sensors in a nanochannel could be advantageous for two reasons:

A) Hydrogen ions produced by polymerase activity from multiple points along the same molecule could be measured simultaneously, ultimately providing long range sequence information.

B) The products of synthesis, hydrogen ions and pyrophosphate, would be highly confined by the nanochannel and would have a higher probability of interacting with the sensor.

A "nanochannel with ISFET detector" device, coupled with the sequencing by idling approach, would have the potential to generate long read length, low error rate sequences from single DNA molecules, whereas other technologies, such as Ion Torrent's, typically require many copies of the molecules.

As an alternative to nanofluidic channels, similar results may be obtained from DNA molecules stretched on a surface, or in a nanoslit. It is possible to generate sequence maps from single molecules of DNA fixed to the surface of a glass slide (Teague, B., M. S. Waterman, et al. (2010). "High-resolution human genome structure by single-molecule analysis." Proc Natl Acad Sci USA 107(24): 10848-10853) or in a nanofluidic channel (Jo, K., D. M. Dhingra, et al. (2007). "A single-molecule barcoding system using nanoslits for DNA analysis." Proc Natl Acad Sci USA 104(8): 2673-2678). By analyzing molecules stretched on to a surface of electronic sensors, it may be possible to detect polymerase idling at a nick, gap, or 3' end. The extra signal created by polymerase idling may enable sequence determination along a single molecule fixed to a surface.

Various fluorescently labeled nucleotides may be used in the current method. In particular, modified nucleotides or nucleotide analogs with four fluorescent groups attached to the different bases have been used for determining the sequence of a template (Seo, T. S., X. Bai, et al. (2004). "Photocleavable fluorescent nucleotides for DNA sequencing on a chip constructed by site-specific coupling chemistry." Proc Natl Acad Sci USA 101(15): 5488-5493). Modified nucleotides or nucleotide analogs similar to these could be used in the present method, with some of the following modifications (see, for example, FIG. 3). First, in some embodiments, chain-terminator nucleotides (such as dideoxy nucleoside triphosphates) are used in the idling step. Second, in some embodiments the fluorescent groups do not need to be cleaved. The fluorescent groups could be attached in a wide variety of ways, and the fluorophores do not need to be cleaved from the nucleobase, as the entire labeled nucleotide will be removed by exonuclease activity. Third, in certain embodiments, the phosphate group may be modified by addition of a quenching group, to quench the fluorescence of the fluorophore. Many useful quenching groups are known in the art, and the quenching group may be attached to a tetraphosphate, pentaphosphate, or hexaphosphate, using chemistry that has been described elsewhere (see, e.g., U.S. Pat. Nos. 7,033,762, 7,223,541, 7,244,566, and 7,256,019 as well as Eid, J., A. Fehr, et al. (2009). "Real-time DNA sequencing from single polymerase molecules." Science 323(5910): 133-138. Thus, the modified nucleotide or nucleotide analog will be quenched prior to incorporation, and will become fluorescent after incorporation, and will remain fluorescent after excision. One potential advantage of the present method is that the modified nucleotides or nucleotide analogs used during the idling step are distinct from those in the extension step, and only the extension nucleotides are incorporated into the growing DNA chain during polymerization. Therefore, the idling mode can use modified nucleotides or nucleotide analogs with modifications that would otherwise inhibit addition of subsequent nucleotides, such as the "virtual terminators" described by Bowers et al. Nature Methods 2009 6:593-595. In these cases the blocking or inhibiting modifications will be removed before incorporation of a (less inhibitory) extension nucleotide.

Exemplary modifications of the chain terminator nucleotides that would block further addition include 2',3'-ddNTPs, 3'-dNTPs, 3'-azido-dNTPs, 3'-amino-dNTPs, 3'-O-methyl-dNTPs or acyclonucleotides (Gardner, A. F. and W. E. Jack (2002). "Acyclic and dideoxy terminator preferences denote divergent sugar recognition by archaeon and Taq DNA polymerases." Nucleic Acids Res 30(2): 605-613). Exemplary modifications of the extension nucleotides include 3'-azidomethyl or 3'-O-allyl.

In some embodiments, the detectable label is attached to the gamma-phosphate of the nucleoside triphosphate, the delta-phosphate of a tetraphosphate, or to any other terminal phosphate of the nucleoside polyphosphate. In some embodiments, a terminally-labeled nucleoside polyphosphate has three, four, five, or more phosphates. In some embodiments, the nucleoside polyphosphate is not terminally-labeled, but rather labeled on an internal phosphate. For example, a nucleoside hexaphosphate may be labeled on the $2^{nd}$, $3^{rd}$, $4^{th}$, or $5^{th}$ phosphate.

The difference between the alpha-R and alpha-S stereoisomers of the thiotriphosphate extension nucleotides may be exploited. The two stereoisomers have been shown to have different sensitivities to various nucleases; for example, the R stereoisomer is believed to be only modestly protective against digestion by T4 DNA polymerase, while the S stereoisomer is thought to be fully protective (see, e.g., Di Giusto, D. and G. C. King (2003). "Single base extension (SBE) with proofreading polymerases and phosphorothioate primers: improved fidelity in single-substrate assays." Nucleic Acids Res 31(3): e7). Similarly, the R stereoisomer is resistant to digestion by Exonuclease III (Yang, Z., A. M. Sismour, et al. (2007). "Nucleoside alpha-thiotriphosphates, polymerases and the exonuclease III analysis of oligonucleotides containing phosphorothioate linkages." Nucleic Acids Res 35(9): 3118-3127) while the S stereoisomer is not. As has been described elsewhere (Yang, supra and references therein), several polymerases including Taq, T4, T7, and *E. coli* Polymerase I were believed to prefer to incorporate the alpha-S thiotriphosphate, inverting the stereocenter to the R-form upon incorporation, and creating resistant linkages. However, these specificities show that it is important to purify the individual stereoisomers, and use a combination which can be incorporated by the polymerase used and resistant to the exonuclease activity used. Notably, Yang, supra, showed that Taq and 9° N polymerases will incorporate either stereoisomer, and thus, the polymerase, alpha-thiotriphosphate stereoisomer, and exonuclease activity can be chosen together to optimize the stability of the growing DNA chain. In some embodiments, a mixture of stereoisomers may be used. For example, if the R stereoisomer is resistant to exonucleolysis and the S is not resistant, and the S is incorporated, the S stereoisomer will act as another idling dNTP, and eventually an S would be incorporated. In this way it may not be necessary to purify the stereoisomers. Alternatively, polymerases may incorporate other exonuclease-resistant modified nucleotides for the extension mode.

Some DNA measurement technologies, such as either the SMRT sequencing system described by Pacific Biosciences and various nanopore sequencing strategies, attach a polymerase to a surface or pore and feed the DNA template through the stationary polymerase during the measurement. If the polymerase is induced to idle at a base, the DNA template will also be held at that position. This could enable extra advantages for measurement. Extra tags from the idling step (comprising fluorescent labels or other types of detectable labels) can be generated by reading one nucleobase several times over using the present method, but it may also be possible to read the same tag or fluorescent label for a longer time. For example, a nanopore sequencing device that detects a label (such as charge blockade labels) could detect DNA sequence in two ways: it could either read the tags released after nucleobase incorporation, or, it may record a blockage of the pore by the charge blockade label when the nascent dNTP is held in the active site, as has been described in U.S. Pat. No. 8,652,779. Inducing idling of the polymerase could help in either method; either more tags will be cleaved and detected per base of template read, or, the polymerase can be induced to idle at a single base for long enough to record signal from the blockade labels corresponding to a particular labeled nucleotide analogue in the active site. Alternatively, other methods for reading single nucleotide sequences using nanowires, nanogaps, tunneling electrodes, nanoknives, nanoneedles, or other nanoscale devices could greatly benefit from the idling polymerase keeping the DNA in place until sufficient data is obtained from that base. Finally, an advantage of polymerase idling is that it will reduce the chances of misreading DNA sequence due to polymerase mis-incorporation of the wrong dNTP. All polymerases have the potential to create sequencing errors by base misincorporation, and these errors are difficult to detect in single-molecule sequencing methods such as Pacific Bioscience SMRT sequencer or various nanopore methods which use a polymerase. However, polymerase idling will allow the polymerase many chances to incorporate the correct base at one position of the template, and the resulting sequence may be more accurate.

Figure 7:
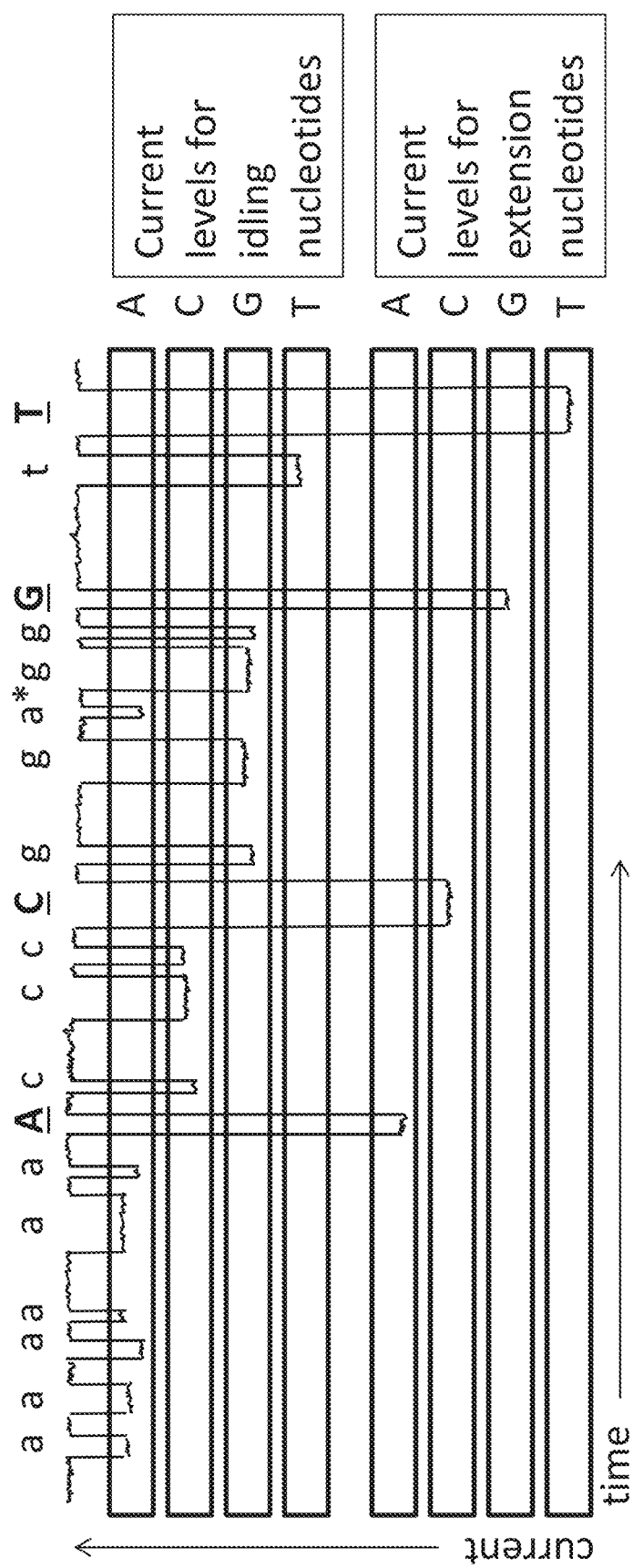
FIG. 7 shows prophetic data that could be obtained from a current-sensing nanopore sequencing device with 8 different tags. This figure provides a current trace and shows how the sequence A, C, G, and T could be read in a sequencing device with 8 different tags distinguishing 4 idling nucleotides and 4 extension nucleotides. The sequence is shown across the top of the diagram; lowercase letters correspond to signals generated during idling, and uppercase letters correspond to signals generated during extension. A mis-incorporation of an adenine nucleotide in idling mode is shown by a *. Note that the sequence could still be determined with high confidence from the idling signals, even if the incorporation of each extension nucleotides generated the same signal.

Additionally, in a nanopore sequencing device, the idling and extension nucleotides could have different tags, creating a total of 8 distinguishable signals for A, C, G, and T chain terminator nucleotides, and A, C, G, and T nuclease resistant nucleotides. In this manner, the incorporation of the extension nucleotide and translocation to the next base would be detected, and homopolymer regions would be easier to sequence accurately. An example of simulated data in this scenario is shown in FIG. 7. Alternatively, if a mixture of chain terminator and nuclease resistant nucleotides is used with a high ratio of chain terminator nucleotides, all four extension nucleotides could share a $5^{th}$ "index" label that could signal translocation to the next base. This embodiment will enable accurate sequencing of homopolymers as long as the concentrations preclude two nuclease resistant nucleotides being added in direct succession. The combination of four labels for chain terminator nucleotides with a $5^{th}$ label for all 4 nuclease resistant nucleotides may be simpler to execute in an optical sequencing device such as the Pacific Biosciences SMRT sequencer.

Figure 3:
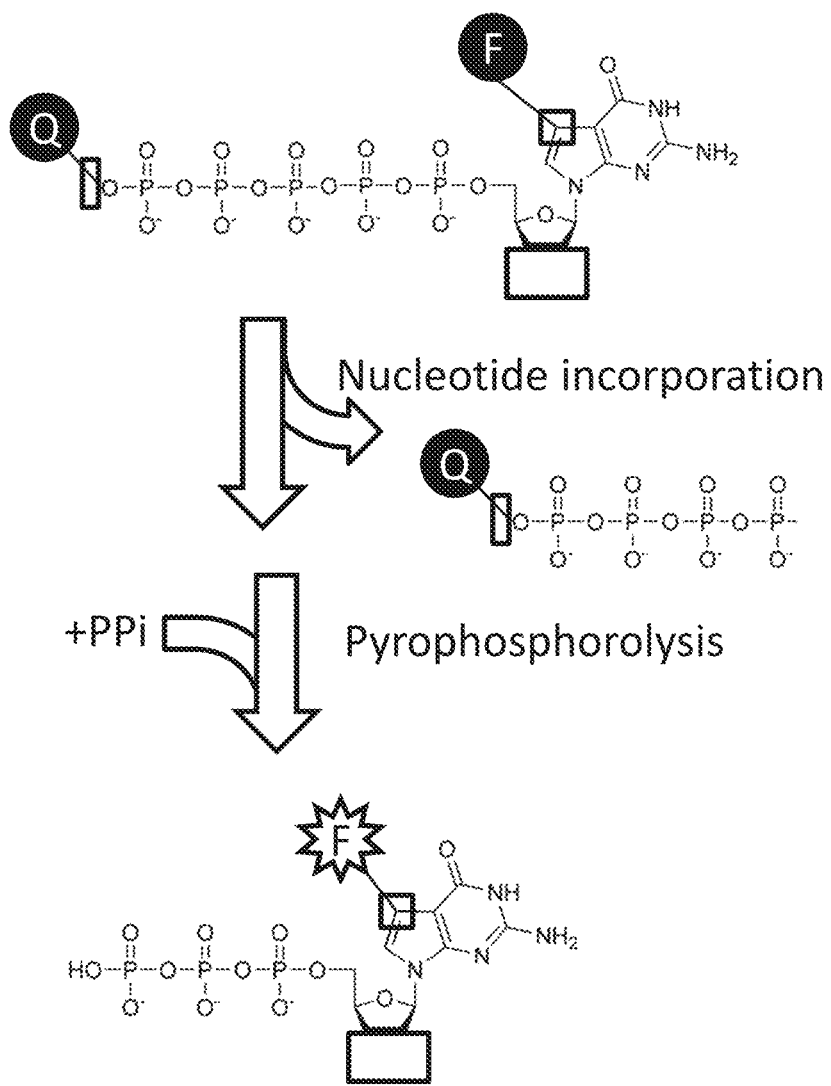
FIG. 3 shows a pyrophosphorolysis method for generating fluorescent byproducts from a fluorophore-quenched chain terminator nucleotide analog.

In an alternative embodiment, the nucleotides could be added by polymerase activity during idling mode and removed by pyrophosphorolysis, in the presence of high concentrations of inorganic pyrophosphate. One example of this embodiment is illustrated in FIG. 3. Pyrophosphorolysis is the reverse reaction of nucleotide addition, and can be driven by relatively high concentrations of inorganic pyrophosphate (in the range of 0.5 to 1.0 mM) (see, e.g., Blasco, M. A., A. Bernad, et al. (1991). "Characterization and mapping of the pyrophosphorolytic activity of the phage phi 29 DNA polymerase. Involvement of amino acid motifs highly conserved in alpha-like DNA polymerases." J Biol Chem 266(12): 7904-7909; Liu, Q. and S. S. Sommer (2002). "Pyrophosphorolysis-activatable oligonucleotides may facilitate detection of rare alleles, mutation scanning and analysis of chromatin structures." Nucleic Acids Res 30(2): 598-604; and Liu, Q. and S. S. Sommer (2004). "Pyrophosphorolysis by Type II DNA polymerases: implications for pyrophosphorolysis-activated polymerization." Anal Biochem 324(1): 22-28). Pyrophosphate is two phosphate molecules bound together by an ester linkage, e.g., the structure $(-2)O_3P—O—PO_3(-2)$. Pyrophosphorolysis consumes the inorganic pyrophosphate and terminal nucleotide, and releases a nucleoside triphosphate. As pyrophosphorolysis can degrade unmodified primer sequences, some other sequencing methods actually describe methods to reduce pyrophosphorolysis (see, for example, US20070172859 and U.S. Pat. No. 7,211,414). However, in the present method, pyrophosphorolysis can be used as an integral part of the idling step, increasing the signal created by the byproducts of nucleotide addition and pyrophosphorolysis. For example, a labeled chain-terminator nucleotide may be added, releasing a quencher attached to terminal phosphate groups. In the presence of a high concentration of inorganic pyrophosphate (PPi, not modified with a quencher), pyrophosphorolysis takes place, removing the labeled nucleotide and generating the labeled nucleoside triphosphate (now absent the quencher.) With each cycle of nucleotide addition by the polymerase and pyrophosphorolysis, a quencher is removed and replaced by PPi, generating a fluorescent nucleoside triphosphate. Typically, the concentrations of PPi will be much higher than the concentration of the quencher-modified phosphate groups, and the concentration of the initial fluor-quencher modified nucleotide will be much higher than the concentration of the unquenched labeled nucleoside triphosphate, so a fluorescent molecule will be generated with each cycle of polymerization and pyrophosphorolysis.

In another embodiment of the polymerase idling method, nucleoside triphosphates created by pyrophosphorolysis may be detected by a reaction inside a microdroplet, as is described by Base4 Innovation Ltd., for example in patent WO 2014/111723 A1.

In another embodiment, the fluorophores are not generated from a quenched-fluorescent nucleotide, but by the use of terminal phosphate-labeled fluorogenic nucleotides (as described in, e.g., Sims, P. A., W. J. Greenleaf, et al. (2011). "Fluorogenic DNA sequencing in PDMS microreactors." Nat Methods 8(7): 575-580 and references cited above). These tetraphosphate fluorophores are only activated when inorganic pyrophosphate is released by the polymerization reaction, and then the phosphate is cleaved by a phosphatase activity.

Exemplary Embodiments

A method for sequencing a nucleic acid is provided. In any embodiment, the method may comprise: (a) obtaining a duplex comprising a nucleic acid and a primer, wherein the primer has a nuclease resistant 3' end; (b) combining the duplex with a chain terminator nucleotide and a polymerase to produce a reaction in which the polymerase idles on the added chain terminator nucleotide by repeatedly adding the chain terminator nucleotide onto the end of the primer using the nucleic acid as a template, and then removing the chain terminator nucleotide; (c) identifying the chain terminator nucleotide added to the end of the primer; and (d) adding a nuclease-resistant nucleotide to the end of the primer after the polymerase has idled on and removed the added chain terminator nucleotide, thereby producing a duplex comprising said template and an extended primer that has a nuclease resistant 3' end.

In any embodiment, the method may comprise: (a) obtaining a duplex comprising a nucleic acid and a primer, wherein the primer has a nuclease resistant 3' end; (b) combining the duplex with a chain terminator nucleotide and a polymerase to produce a reaction in which the polymerase idles on the added chain terminator nucleotide by repeatedly adding the chain terminator nucleotide onto the end of the primer using the nucleic acid as a template, and then removing the chain terminator nucleotide; (c) identifying the chain terminator nucleotide added to the end of the primer; and (d) adding a nuclease-resistant nucleotide to the end of the primer after the polymerase has idled on and removed the added chain terminator nucleotide, thereby producing a duplex comprising said template and an extended primer that has a nuclease resistant 3' end, wherein step (d) may be simultaneous with, or may precede step (c).

In any embodiment, the method may further comprise repeating steps (b) and (c) on the product of step (d), thereby determining the sequence of two consecutive nucleotides of the nucleic acid.

In any embodiment, the nuclease-resistant nucleotide of (d) may be a reversible chain terminator and wherein the method comprises, after step (d), removing a blocking moiety from the nuclease resistant nucleotide before repeating step (b).

In any embodiment, the method may comprise repeating steps (b), (c) and (d) at least 10 times, thereby determining the sequence of at least 10 consecutive nucleotides in the nucleic acid.

In any embodiment, the method may comprise combining said duplex with the chain terminator nucleotide, the proofreading polymerase and the nuclease-resistant nucleotide, wherein the chain terminator nucleotide is in a molar excess relative to the nuclease-resistant nucleotide.

In any embodiment, the method may comprise quantifying the number of idling cycles by measuring how much chain terminator is added to the end of the primer by the polymerase.

In any embodiment, the combining step (b) may comprise combining the duplex with a single chain terminator corresponding to G, A, T or C.

In any embodiment, the identifying step may comprise detecting pyrophosphate release.

In any embodiment, the identifying step may comprise direct or indirect measurement of pH.

In any embodiment, the chain terminator nucleotide may be a terminal phosphate labeled fluorescent nucleotide and the identifying step comprises reading fluorescence.

In any embodiment, the chain terminator nucleotide may be a phosphate labeled fluorescent nucleotide, which may be labeled on a phosphate which is not the terminal phosphate, and the identifying step comprises reading fluorescence.

In any embodiment, the chain terminator nucleotide may be a fluorescent nucleotide that comprises a quencher on a terminal or an internal phosphate, and the identifying step comprises reading fluorescence.

In any embodiment, the combining step (b) may comprises: combining the duplex with four chain terminators corresponding to G, A, T and C, wherein the four chain terminators comprise different distinguishable labels; and the identifying step (c) may comprise identifying which of the four chain terminator nucleotides is added to the end of the primer.

In any embodiment, the distinguishable labels may comprise fluorescence labels.

In any embodiment, the distinguishable labels may comprise charge blockade labels.

In any embodiment, the identifying step may comprise use of a nanopore or nanogap detector.

In any embodiment, the identifying step may comprise measurement of ionic current through a nanopore.

In any embodiment, the identifying step may comprise measurement of fluorescence in conjunction with translocation of DNA through a nanopore.

In any embodiment, the identifying step may comprise an electronic measurement such as tunneling current.

In any embodiment, the nuclease-resistant nucleotide may contain a phosphorothioate.

In any embodiment, the duplex may be DNA that comprises single stranded regions and double stranded regions, that has been stretched on a substrate.

In any embodiment, the duplex may be in a nanofluidic channel on a substrate.

In any embodiment, the duplex may be made by: nicking a double stranded DNA at one or more sites, making single stranded gaps in the double stranded DNA using an exonuclease, adding an alpha-thio reversible terminator onto 3' ends adjacent to the gaps, and then deprotecting the added alpha-thio reversible terminators. In these embodiments, the exonuclease may be ExoIII.

In any embodiment, the nucleic acid or the primer may be immobilized on a solid support.

In any embodiment, the DNA polymerase may be a proofreading polymerase.

In any embodiment, the identifying step (c) may comprise use of a nanopore. The nanopore may be used to detect ionic current changes affected by natural or modified nucleotides or nucleotide analogues. In any embodiment, the nanopore may be used together with detection of fluorescent labels on nucleotides or chemical groups such as polyphosphates released during nucleotide addition. In any embodiment, the nanopore may be a protein nanopore in a biological membrane, a protein nanoproe in a synthetic membrane, or a synthetic nanopore, e.g., a solid state pore in a silicon nitride membrane.

In any embodiment, the combining step may comprise a pyrophosphorolysis reaction.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of sequencing DNA, comprising:
   (a) obtaining a duplex comprising a nucleic acid and a primer;
   (b) combining the duplex with one or more nucleoside polyphosphates, one or more chain terminator nucleotides, a DNA polymerase, and inorganic pyrophosphate to produce a reaction in which the polymerase repeatedly adds a chain terminator nucleotide onto the end of the primer using the nucleic acid as a template, and then removes the chain terminator nucleotide by pyrophosphorolysis; and
   (c) identifying the chain terminator nucleotide added to the end of the primer;
   wherein:
   i) the probability of incorporating a chain terminator nucleotide is greater than the probability of incorporating a nucleoside polyphosphate.

2. The method of claim 1, wherein identifying step (c) involves measuring the products of the pyrophosphorolysis reaction.

3. The method of claim 1, wherein the identifying step (c) occurs in real time.

4. The method of any claim 1, further comprising determining the sequence of at least 10 consecutive nucleotides in the nucleic acid.

5. The method of claim 1, wherein the chain terminator nucleotide comprises a label.

6. The method of claim 5, wherein the method comprises quantifying how much chain terminator nucleotide is added to the end of the primer by the polymerase.

7. The method of claim 5, wherein the label is a fluorescent label.

8. The method of claim 1, wherein the polymerase lacks exonuclease activity.

9. The method of claim 1, wherein the identifying step comprises direct or indirect detection of protons.

10. The method of claim 5, wherein the label is attached to a terminal phosphate.

11. The method of claim 5, wherein the label comprises a charge blockade label, and the identifying step comprises use of a nanopore.

12. The method of any claim 1, wherein:
the combining step (b) comprises combining the duplex with four chain terminators corresponding to G, A, T and C, wherein the four chain terminators comprise different distinguishable labels; and
the identifying step (c) comprises identifying which of the four chain terminator nucleotides is added to the end of the primer.

13. The method of claim 1, wherein the chain terminator nucleotide comprises a fluorescence quencher.

14. The method of any claim 1, wherein the chain terminator nucleotide is a dideoxynucleotide.

15. The method of claim 1, wherein the primer is extended by more than one nucleotide in step (b).

16. The method of claim 1, wherein the nucleoside polyphosphates are nucleoside triphosphates.

17. The method of any claim 12, further comprising determining the sequence of 10 or more consecutive nucleotides.

18. The method of claim 12, wherein the identifying step (c) comprises use of a nanopore.

19. The method of any claim 1, wherein the nucleic acid or the polymerase or the primer is immobilized on a solid support.

20. The method of any claim 5, wherein the nucleoside polyphosphates comprise a label.

* * * * *